US00PP09999P

United States Patent [19]

Avila

[11] Patent Number: Plant 9,999

[45] Date of Patent: Aug. 12, 1997

[54] ILEX PLANT VARIETY NAMED "MONDO"

[75] Inventor: Rosendo Avila, Azusa, Calif.

[73] Assignee: Monrovia Mursery Company, Azusa, Calif.

[21] Appl. No.: 612,818

[22] Filed: Mar. 11, 1996

[51] Int. Cl.[6] ..... A01H 5/00

[52] U.S. Cl. ..... Plt./65

[58] Field of Search ..... Plt./65

*Primary Examiner*—James R. Feyrer
*Assistant Examiner*—Melissa L. Kimball
*Attorney, Agent, or Firm*—Christie, Parker & Hale, LLP

[57] ABSTRACT

A new and distinct Ilex plant variety having dwarf, compact growth habit.

1 Drawing Sheet

BACKGROUND OF THE INVENTION

The present invention relates to a new and distinct variety of Ilex which was discovered as a mutation in a controlled planting of the Ilex variety 'Blue Boy', U.S. Pat. No. P.P. 2,435, in Azusa, Calif. The varietal denomination of the new variety is 'Mondo'.

SUMMARY OF THE INVENTION

The new variety is distinguished from its parent and other known commercial varieties of which I am aware in its growth habit and foliage. It differs from its parent 'Blue Boy' in having a more compact, dwarf growth habit, shorter and more numerous and regular branching pattern, numerous leaves which are about one half the size of its parent or smaller densely arranged along the stem. In addition, the foliage of the new variey exhibits a brighter green leaf color for mature leaves, and a lighter and more uniform Winter leaf color. Flower clusters are not prominent in the Winter season.

Asexual reproduction by vegetative cuttings and micro-proagation in Azusa, Calif., has confirmed that the combination of characteristics of the new variety as herein disclosed are firmly fixed and retained through successive generations of asexual reproduction.

DESCRIPTION OF ILLUSTRATIONS

The new variety of Ilex is illustrated in the accompanying illustration which shows typical plant characteristics and stems of 'Mondo' as compared to its parent 'Blue Boy', with colors being as nearly true as is possible for illustrations of this type.

DETAILED DESCRIPTION OF THE NEW VARIETY

The following is a detailed description of the new cultivar of Ilex as observed in Azusa, Calif. in the months of May and February. The color designations indicated are in accordance with The Royal Horticultural Society Colour Chart by color plant designations. Phenotype expression may vary with variations in environment such as temperature, light, intensity, day length, growing and cultural conditions.

Botanical classification: Ilex (Holly).
Origin: Mutation of Ilex 'Blue Boy'.

PLANT

A. Form: Dwarf, compact, rounded, evergreen shrub, about 3 feet high and wide.

B. Growth: Uniform and freely branching, slow growing.

C. Foliage:

*Size.*—Length: About ¾ to 1¼ inches. Width: About ½ to 1 inch.

*Quantity.*—Abundant, densely spaced about ¼ inch apart along stem.

*Color.*—New foliage (Spring/Summer): Upper side: Near 151A. Underside: Near 149C. Old Foliage (Spring/Summer): Upper side: Near 139A. Underside: Near 146B. New Foliage (Winter): Upper side: Near 187A and near 202A. Underside: Near 187B with tinge of green. Old Foliage (Winter): Upper side: Near 187A and near 202A, leaves further down on stem and more protected from cold and sunlight fade to near 139A. Underside: Near 187B, leaves further down stem and more protected from cold and sunlight fade to blotched purple near 187B and near 149C.

*Shape.*—Elliptical; tip acute; base is rounded.

*Texture.*—Upper side: Coriaceous, shiny. Underside: Coriaceous, dull.

*Veination.*—Prominent midrib, branching lateral veination.

*Edge.*—Serrate, undulating.

*Serration.*—Distinct, regular, pointed; no end spine.

*Petiole.*—Smooth and short about ⅛ to 3/16 inch; some are slightly curved.

*Stems and petiole color.*—Upper side near 187A in warm season, blacker in Winter; underside near 146B.

*Stipules.*—None — regular petiole.

*Auricle.*—Not present, simple leaves.

*Rachis.*—Not present.

*Resistance to disease.*—Not generally susceptible to any diseases.

D. Wood:

*New shoots.*—Smooth and slightly glossy; near 187A.

*Old wood.*—Slight irregular corky ridges, near 146B.

*Internode.*—Very short about ⅛ inch.

E. Winter hardiness: Winter hardy to USDA zone 4 (−30° F.).

F. Comparison with Characteristics of 'Blue Boy':

| | ILEX 'MONDO' | ILEX 'BLUE BOY' |
|---|---|---|
| HEIGHT & SPREAD | 3' × 3' (to date) | 15' h × 12' w |
| HABIT | Dwarf, compact shrub | Large, upright shrub |
| BRANCHES | Short, numerous, regular pattern | Long, average number, wide pattern |
| LEAVES | Numerous, densely arranged along stem | Average number, wider spacing |
| LEAF SIZE | ½ or less of 'Blue Boy' | Typical for Holly |
| MATURE LEAF COLOR | Brighter green | |
| FLOWER | Flower cluster not prominent in Winter | Very prominent in Winter |

REPRODUCTIVE ORGANS AND FLOWER

A. Stamens, filaments and anthers:

*Arrangement.*—Four even spaced and arranged around center of flower (styles not present).

*Color.*—Stamens: White. Filaments: White. Anthers: Yellow.

B. Pollen:

*Color.*—Yellow.

C. Styles: Generally none, occasionally present — yellow (primarily male flowers).

D. Stigmas: Generally none, occasionally present — yellow.

E. Fruit (Rare): Seldom seen, an occasional red berry-like drupe resulting from few flowers.

*Shape.*—Globular, round.

*Size.*—About ¼ inch diameter.

*Color.*—Red.

*Seeds.*—Seeds do not protrude.

F. Petals:

*Color.*—Pure white, slight rose tinge on underside.

*Size.*—About ⅛ inch long, (entire corolla about ¼ inch diameter).

*Shape.*—Rounded.

I claim:

1. A new variety of Ilex plant substantially as herein shown and described.

* * * * *

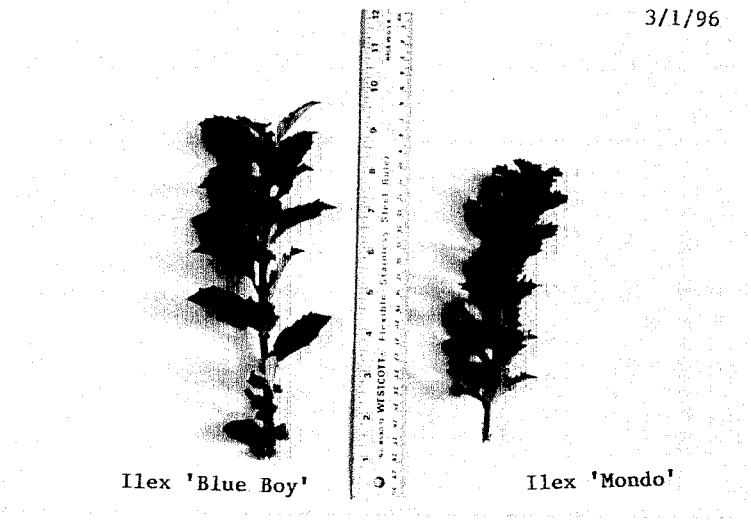
3/1/96
Ilex 'Blue Boy'
Ilex 'Mondo'
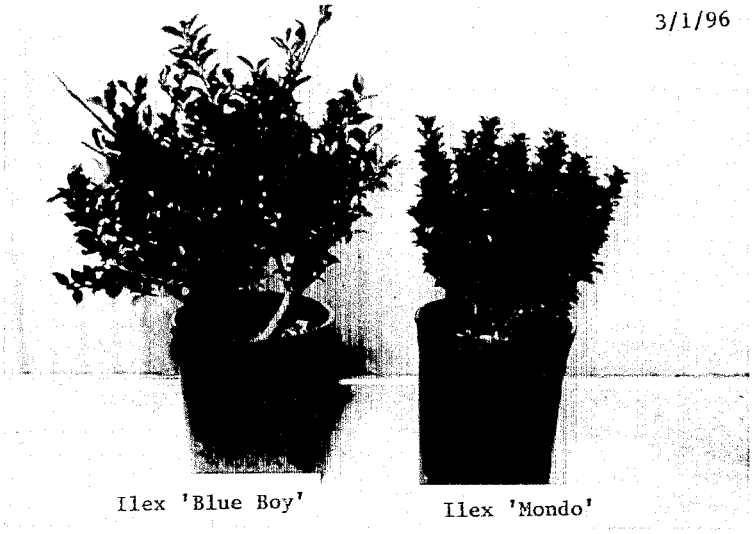
3/1/96
Ilex 'Blue Boy'
Ilex 'Mondo'

UNITED STATES PATENT AND TRADEMARK OFFICE

CERTIFICATE OF CORRECTION

PATENT NO. : Plant 9,999
DATED : August 12, 1997
INVENTOR(S) : Rosendo Avila

It is certified that error appears in the above-indentified patent and that said Letters Patent is hereby corrected as shown below:

Item [54], the title should read
-- ILEX PLANT VARIETY NAMED 'MONDO' --

Column 1, line 32, change "illustration" to -- illustrations --.

Signed and Sealed this

Twenty-fourth Day of February, 1998

*Attest:*

Bruce Lehman

BRUCE LEHMAN

*Attesting Officer*

*Commissioner of Patents and Trademarks*